United States Patent
Hatasaka, Jr. et al.

(10) Patent No.: US 6,537,285 B1
(45) Date of Patent: Mar. 25, 2003

(54) SPIRAL CERVICAL RETRACTOR APPARATUS

(75) Inventors: Harry H. Hatasaka, Jr., Park City, UT (US); Richard Crangle, Salt Lake City, UT (US)

(73) Assignee: University of Utah, Salt Lake City, UT (US)

( * ) Notice: Subject to any disclaimer, the term of this patent is extended or adjusted under 35 U.S.C. 154(b) by 0 days.

(21) Appl. No.: 09/777,136

(22) Filed: Feb. 5, 2001

Related U.S. Application Data (60) Provisional application No. 60/180,432, filed on Feb. 4, 2000.

(51) Int. Cl.[7] .............................................. A61B 17/42
(52) U.S. Cl. ....................... 606/119; 600/201; 600/210; 600/217
(58) Field of Search ...................... 606/119; 600/114, 600/184, 188, 201–205, 210, 217

(56) References Cited

U.S. PATENT DOCUMENTS

| | | | | |
|---|---|---|---|---|
| 5,195,964 A | * | 3/1993 | Kletzky et al. | 604/55 |
| 5,437,266 A | * | 8/1995 | McPherson et al. | 600/217 |
| 5,577,993 A | * | 11/1996 | Zhu et al. | 600/204 |
| 5,976,079 A | * | 11/1999 | Volz et al. | 600/209 |
| 5,980,534 A | * | 11/1999 | Gimpelson | 606/119 |
| 6,206,827 B1 | * | 3/2001 | Chin et al. | 600/217 |

* cited by examiner

Primary Examiner—Kevin Shaver
Assistant Examiner—Michael B Priddy
(74) Attorney, Agent, or Firm—Morriss, Bateman, O'Bryant & Compagni (57) ABSTRACT

A spiral cervical retraction apparatus is provided to straighten out the canal to the uterus during a medical procedure which allows for placement of instruments into the cavity of the uterus such as artificial insemination devices, curettes, biopsy instruments, and radiologic devices to instill dye. The apparatus includes a rigid tube for traction assisted insertion and removal of instruments by a screw-like action. A spiral wire is secured to the tip of the device for insertion into the cervix of a patient. Preferably, the apparatus has a substantially rigid handle tor twisting the spiral tip.

39 Claims, 4 Drawing Sheets

SPIRAL CERVICAL RETRACTOR APPARATUS

This application claims the benefit of Provisional Application No. 60/180,432, filed Feb. 4, 2000.

BACKGROUND OF THE INVENTION

1. The Field of the Invention

The present invention relates generally to medical instruments used to access the cavity of the uterus. More particularly, it concerns a cervical retractor apparatus to assist placement of other instruments into the cavity of a uterus, or to better visualize the cervix or upper vagina for the purposes of colposcopy and/or biopsy. The apparatus will also provide intraperitoneal retraction and exposure via laparoscopy.

2. The Background Art

It is common practice to place traction on the cervix during various medical procedures to straighten out the uterus. In gynecology, the need often arises to place instruments into the cavity of the uterus (e.g., artificial insemination devices, curettes, biopsy instruments, and radiologic devices to instill dye). Unfortunately, the canal of the uterine cervix is often curved such that placing an instrument into the uterus is difficult. By placing traction on the cervix, the canal may be straightened out so that instruments can then be more easily introduced. The most common instrument used to grasp the cervix is a tenaculum. A tenaculum is a self-retaining ratcheting stainless steel instrument with two or more sharp points that actually pierce the cervix in order to grasp the cervix. A tenaculum is typically used in an operating room setting when the patient is anesthetized. The tenaculum is used to apply a great amount of counter-traction on the cervix so that dilators can be passed into the cervix to widen the opening in order to pass larger instruments into the uterus.

Problems with the tenaculum include the relatively large diameter points on the "tong" portion which frequently cause bleeding and may require suturing to stop the bleeding. Also, application by the physician of excessive traction can pull off cervical tissue causing lacerations. Despite such problems, the tenaculum is preferred over clamping devices because the latter tend to slip off, lacerate large portions of the cervix, or crush and devitalize the tissue. While cervical infections are quite rare with the use of a tenaculum, in the awake patient, as the tenaculum pierces and compresses the cervix, considerable cramping and discomfort are often experienced by the patient.

Most gynecologists frequently use a tenaculum in the office, and thus keep a supply of them. A speculum is first inserted into the vaginal opening to hold open the surrounding tissue to allow access to and visualization of the cervix of the patient. If the tenaculum is to be used on an awake patient, the local area of the cervix is most often infiltrated first with a local anesthetic via a small gauge needle. A tenaculum in an outpatient awake setting may be utilized to:

1. Introduce Pipelle®-and other brand suction aspirators;
2. Introduce curettes;
3. Facilitate office hysteroscopy;
4. Perform difficult intrauterine inseminations;
5. Sound (measure) the uterine cavity;
6. Facilitate hysterosalpingography;
7. Perform difficult transfer of embryos;
8. Stabilize the cervix for biopsy;
9. Provide exposure for colposcopy; and
10. Facilitate paracervical anesthetic blocks.

In advanced reproductive technology such as in vitro fertilization, a critical step in the process is placement of embryos directly into the uterine cavity. It is believed that the more bleeding and cramping that is caused by this procedure, the less the pregnancy implantation rate. Therefore, the use of the tenaculum during in vitro fertilization procedures has been shunned. Instead, thin catheters of various designs and flexibility have been manufactured to pass the embryos directly into the uterus without the need to manipulate the cervix or uterus. Another approach has been to utilize a small suture through the lip of the cervix using a tiny atraumatic curved needle to pierce the cervix. The use of such a small suture has proved to cause less bleeding and cramping compared to performing the procedure with a tenaculum. Using a suture to pierce the cervix, however, is quite cumbersome and requires a needle driver.

A skin hook (e.g., a Cottle Skin Hook manufactured by MILTEX in Lake Success, N.Y.) is another device that may be employed for insertion through the cervix to perform some of the above-discussed procedures. A skin hook, however, has several drawbacks. First, the handle of a typical skin hook is too short to properly reach into the vagina. In addition, there is no way to keep the skin hook in place, requiring continuous traction. Moreover, the angle of the hook is such that it can often be applied but cannot be readily removed due to the restricted mobility when the skin hook is used in the confines of the vagina.

Some of these same problems confront the gynecologist when using a tenaculum. For example, in order to maintain proper traction on the cervix, either the gynecologist must hold the tenaculum with one hand while performing the desired procedure with the other hand or an medical assistant must be present to hold the tenaculum in place while the gynecologist performs procedures that require both hands. In many situations, it is not convenient to require the help of a medical assistant and it may not be easy to perform the desired procedure with one hand. In either case, it may not be desirable to vary the amount of traction on the cervix depending on the amount of force applied by the hand of either the gynecologist or the medical assistant.

Thus, it would be advantageous to provide an apparatus that can be utilized to perform the previously mentioned procedures as well as other procedures where retraction of the cervix is desired, that produces only one puncture site in the cervix, has self-retention capabilities, that substantially eliminates tissue compression, and minimizes bleeding, infection potential, and other types of trauma to the cervix.

OBJECTS AND SUMMARY OF THE INVENTION

It is an object of the present invention to provide a cervical retractor that causes minimal pain, bleeding and cramping.

It is another object of the present invention to provide a cervical retractor which is simple in design and easy to manufacture.

It is a further object of the present invention to provide a cervical retractor that is disposable in whole or in part.

It is another object of the present invention to provide a cervical retractor capable of placing instruments into a patient's uterus cavity.

It is a further object of the present invention to provide a cervical retractor which is portable and capable of being carried and operated by hand.

It is yet another object of the present invention to provide a cervical retractor that illuminates the cervix and/or surrounding tissue.

It is still another object of the present invention to provide a cervical retractor that may also provide a lavage or suction & injection of medication.

It is yet another object of the present invention to provide a cervical retractor that is attachable to a standard speculum to facilitate a variety of procedures.

It is still another object of the present invention to provide a cervical retractor that allows visualization of the procedure site. Another object of the present invention is to provide a spiral retractor for use through a laparoscope allowing retraction with self-retention for the purpose of exposure and visualization of such organs as the uterus and ovaries.

The above objects and others not specifically recited are realized in specific illustrative embodiments of a spiral cervical retractor.

In accordance with the present invention, an apparatus for insertion into and removal from the cervix of a patient comprises a wire tipped device, the wire preferably having a spiral or curved configuration. The cervical retractor preferably includes a substantially elongated handle sized to fit within the vagina of a patient, having a spiral wire or hook associated with a distal end of the handle and means for rotating the spiral wire associated with the proximal end of the handle.

The elongated handle is preferably comprised of a substantially rigid traction type handle that may be held in a substantially stationary position relative to the vagina of a patient. Moreover, the means for rotating the spiral wire may comprise a knob or gripping portion rotatably associated with the proximal end of the handle and that is coupled or linked to the spiral wire such that rotation of the knob results in corresponding rotation of the spiral wire.

The spiral wire is preferably of a size and material that will provide relatively high tensile strength while having at least some lateral flexibility.

In a preferred embodiment, the cervical retractor is made of made of relatively inexpensive materials, such as plastics, and is intended to be disposable or easily sterilized after each use.

In yet another preferred embodiment, the spiral tip of the cervical retractor is removable from the handle of the cervical retractor and is intended to be disposable.

In a preferred embodiment, the cervical retractor in accordance with the principles of the present invention includes a cannula that extends the length of the handle and is configured for receiving therein a fiber optic strand for illuminating the site surrounding the cervix of the patient.

In still another preferred embodiment, the cervical retractor includes an elongate cannula configured for connecting to an external device to provide a lavage or suction at the distal end of the cervical retractor as desired.

In yet another preferred embodiment, the cervical retractor in accordance with the principles of the present invention include a device proximate the distal end of the cervical retractor for visualization of the site surrounding the cervix.

In yet another preferred embodiment, the cervical retractor in accordance with the principles of the present invention include a plurality of cannulas through which a plurality of procedures may be performed and a plurality of devices may be inserted.

In still another preferred embodiment, the cervical retractor in accordance with the principles of the present invention comprises an elongate tube housing a retractable rod therein. The retractable rod is provided with a sharpened spiral wire at one end and a hand or gripping portion for manipulation by the gynecologist or other health care professional at the other.

In another preferred embodiment, the retractable rod is biased relative to the tube so that the spiral wire is pulled back into the tube.

In yet another preferred embodiment, the cervical retractor includes an attachment mechanism for grasping a portion of a speculum in order to hold the cervical retractor in place.

In yet another preferred embodiment, the tube of the cervical retractor is configured to receive therein various other devices, for example, a fiber optic strand for providing illumination, a camera lens for visualization, or other instrument housed at least partially within the tube for performing a function at the distal end of the retractor.

Additional objects and advantages of the invention will be set forth in the description which follows, and in part will be apparent from the description, or may be learned by the practice of the invention without undue experimentation. The objects and advantages of the invention may be realized and obtained by means of the instruments and combinations particularly pointed out in the appended claims.

BRIEF DESCRIPTION OF THE DRAWINGS

The above and other objects, features and advantages of the invention will become apparent from a consideration of the subsequent detailed description presented in connection with the accompanying drawings in which.

DETAILED DESCRIPTION

For the purposes of promoting an understanding of the principles in accordance with the invention, reference will now be made to the embodiments illustrated in the drawings and specific language will be used to describe the same. It will nevertheless be understood that no limitation of the scope of the invention is thereby intended. Any alterations and other modifications of the inventive features illustrated herein, and any additional applications of the principles of the invention as illustrated herein, which would normally occur to one skilled in the relevant art and having possession of this disclosure, are to be considered within the scope of the invention claimed.

A spiral cervical retraction apparatus in accordance with the present invention is capable of inserting medical devices into the uterus as well as placing traction on the cervix. As hereinafter described, a preferred embodiment includes a cervical retractor with a spiral hook on one end thereof configured for placing traction on the cervix while allowing insertion of other medical instruments through the vaginal cavity.

Figure 1:
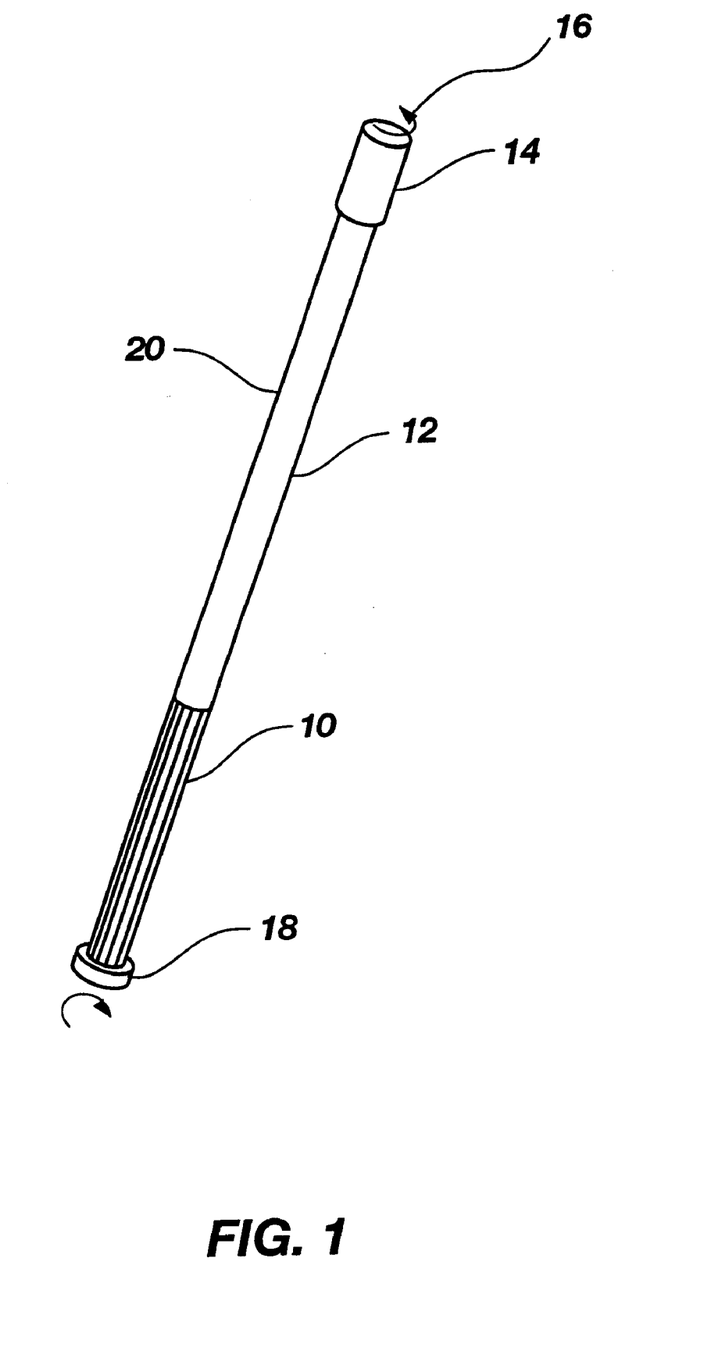
FIG. 1 is a perspective side view of first preferred embodiment of a cervical retractor in accordance with the is principles of the present invention.

Referring to FIG. 1, a spiral wire-tipped device 20 is configured for insertion into a body cavity and removal therefrom such as the vagina of a patient. The spiral wire-tipped device 20 includes an elongated substantially rigid handle or tube 12 having a spiral needle-hook 16 secured thereto proximate the sheath. In a reusable configuration, the handle 12 may be comprised of stainless steel. The handle 12 may also be formed from a plastic or other material known in the art so that the handle 12 is disposable. Regardless of the material, it is preferable that the tube 12 be rigid enough to enable cervical retraction without binding or popping.

The spiral hook 16 is configured to be rotatable relative to the traction manipulation handle portion 10 as with a rotating knob 18 rotatably secured to the proximal end of the manipulation handle 10. The hook 16 may be comprised of a solid wire or a hollow needle to allow for injection of anesthetics or other medicines into or around the cervix. The hook 16 is preferably formed into a spiral shape or otherwise curved to be relatively easily insertable into the cervix of a patient upon rotation of the knob 18 at the proximal end of the handle 12.

In a preferred embodiment, the spiral hook 16 is spring loaded and retractable into the sheath 14. Retraction of the spiral hook 16 provides a safety feature to prevent inadvertent punctures during insertion of the device 20 into the vagina and for operator safety after the spiral wire 16 has been contaminated with bodily fluids.

The cervical retractor 20 in accordance with the present invention reduces the risk of introducing cervical infections compared to other devices known in the art since the cervical retractor 20 of the present invention will be negligible since any punctures caused by the cervical retractor 20 are small. In addition, the cervical retractor 20 can easily place traction on the cervix with little, if any, trauma inflicted upon the cervix. As infection is rarely seen with the multi-pronged, large tenaculums, infection is even less likely with use of the cervical retractor 20 of the present invention. Moreover, devices, such as fetal scalp electrode devices, have been employed with excellent results in obstetrics. The cervical retractor in accordance with the principles of the present invention is sterile, disposable or reusable, easy to apply (even blindly by feel alone), easy to remove, and relatively strong to be able to manipulate the cervix and to apply proper traction as desired. In addition, the likelihood of the spiral hook 16 breaking off in the cervical tissue is quite low. Likewise, as previously discussed, the relatively small puncture site caused by the spiral hook 16 significantly decreases the likelihood of significant bleeding, reduces the pain of such traction procedures and, as a result, reduces the amount of cramping caused by such procedures.

Compared to fetal scalp electrodes known in the art, which are designed to transmit fetal electrical cardiac activity signals via wires not to obtain traction, a slightly heavier spiral wire 16 is employed with the cervical retractor 20 of the present invention to allow sufficient cervical traction. Moreover, the cervical retractor 20 is not intended to completely replace the tenaculum in situations where significant amounts of traction need to be generated under anesthesia. As previously discussed, the tenaculum is typically an operating room instrument that has been used, unmodified, in unanesthetized clinic situations for lack of an alternative. The cervical retractor 20 in accordance with the present invention is capable of straighten the cervical canal by stretching the uterus under traction. This is achieved with the cervical retractor 20 with far less force than required when using a tenaculum for cervical dilatation. Indeed, the spiral wire 16 may comprise a relatively small, high tensile strength wire, comparable to a 3-0 suture, to sufficiently straighten the cervical canal without risking wire breakage within the cervix.

The rigid handle 12 of the present invention for traction is also beneficial as it will facilitate insertion and removal of the spiral wire 16 by a screw-like action. The fetal scalp electrode previously discussed, however, is not suitable for applications such as embryo transfer because on a mobile cervix a hand must be placed into the vagina to stabilize the tip of the electrode for accurate placement. Such manual manipulation is both highly uncomfortable to the patient and extremely inconvenient. Furthermore, fetal scalp electrodes are removed either by directly unscrewing the spiral tip from the scalp once the baby is delivered, or, if the baby is unborn, the two electrode wires are pulled apart which causes the spiral tip to spin in a counterclockwise direction which unscrews the device from the scalp. The present invention provides a much easier means for removal of the spiral wire 16 as the rigid handle 12 can directly twist the spiral tip in and out since the device is not intended to remain in place for long periods of time as is the fetal scalp electrode. Like the fetal scalp electrodes which remain in place remarkably well despite the rigors of labor, and unlike skin hooks, the spiral cervical retractor is self-retaining by providing a hook or some other structure on the handle 10 for hooking onto the edge of the speculum, and therefore frees up both hands of the operator until traction is required. The instrument can then be placed under traction with the non-dominant hand while the operating instrument (i.e. catheter, curette, etc.) is passed into the uterus with the dominant hand. This is similar to the way the tenaculum is currently used. Application of this device, however, will be much easier and quicker than placing a suture and much less painful and traumatic than a tenaculum.

The cervical retractor 20 in accordance with the present invention could be made disposable, or as a permanent sterilizable instrument. The permanent model may be comprised of a lightweight reusable sterilizable handle with a female threaded end to accept disposable plastic male threaded tips that house the spiral wire 16. By using disposable tips, the wire hook 16 is assured to be sharp and sterile with each use. As previously discussed, a modification of the spiral cervical retractor which may prove advantageous will be to have a hollow sleeve surrounding a solid-core handle such that the spiral tip can be rotated by rotating a knob 18 at the external end of the instrument 20. This would allow the handle 12 to remain stationary while the wire spiral 16 is rotated into the cervix.

Figure 2:
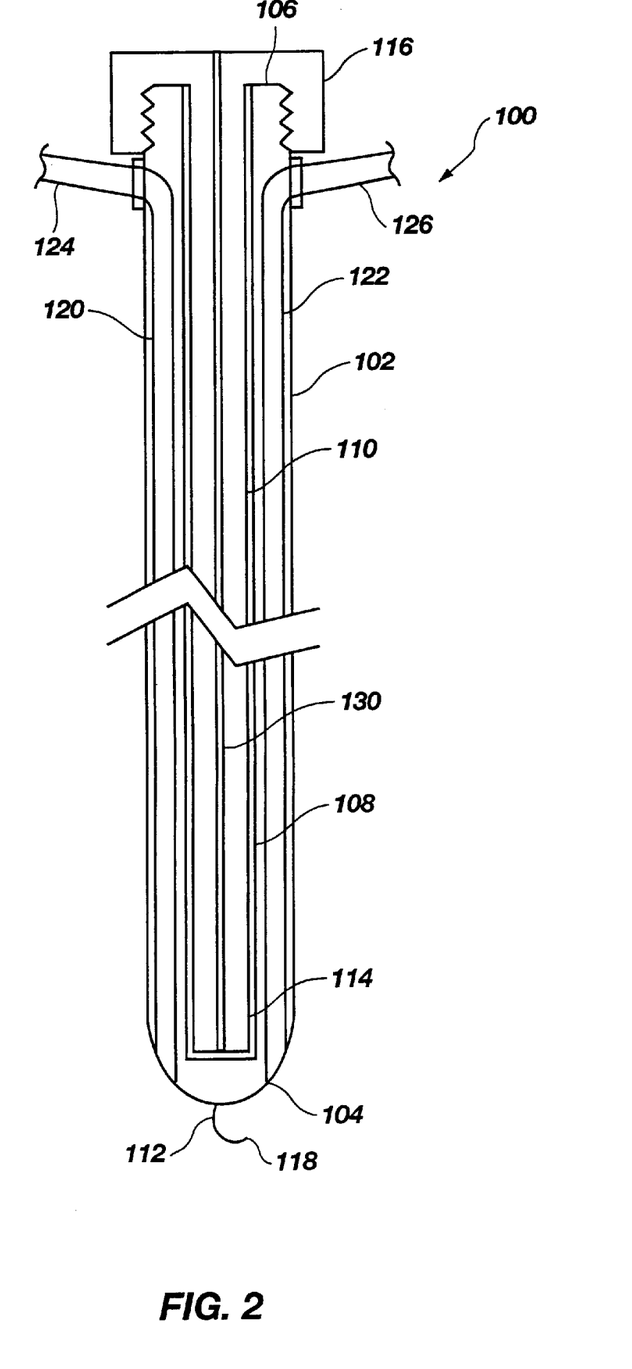
FIG. 2 is a cross-sectional side view of a second embodiment of a cervical retractor in accordance with the principles of the present invention.

FIG. 2 illustrates another preferred embodiment of a spiral cervical retractor, generally indicated at 100, in accordance with the principles of the present invention. The cervical retractor 100 is comprised generally of an elongate outer housing 102 having a distal end 104 and a proximal end 106. The housing 102 defines a first longitudinal chamber 108 therein into which an elongate shaft 110 is inserted. The elongate shaft 110 includes a spiral hook 112 attached to a distal end 114 thereof. The spiral hook 112 is configured to have sufficient strength to perform cervical retraction. The shaft 110 is coupled to the proximal end 106 of the housing 102 as with a threaded coupling device 116 such that rotation of the coupling device 116 retracts or extends the spiral hook 112 into and out of the housing 102. Likewise, rotation of the coupling device 116 causes the spiral hook 112 to rotate relative to the housing 112. Moreover, as the spiral hook 112 is extended, it rotates in a direction such that the tip 118 of the hook 112 can penetrate tissue that it contacts.

The housing 102 is also provided with one or more longitudinally extending lumens or cannulas, such as cannulas 120 and 122, that extend from proximate the proximal end 106 of the housing 102 to its distal end 104. The cannulas 120 and 122 may be configured for performing various functions. For example, the cannulas 120 and 122 may be connected to tubes 124 and 126, respectively, for providing a lavage and suction at the distal end 104 of the housing 102. Likewise, the cannulas 120 and 122 may contain fiber optic elements 124 and 126 for providing a light source and a camera lense, respectively, at the distal end 104. The cannulas 120 and 122 may be configured and/or used for many other medical procedures known in the art including but not limited to a receiving a rotating magnifying eye piece to enhance visualization of the procedure site and/or small operating instruments for local operative work on the cervix.

As further illustrated in FIG. 2, an elongate lumen 130 extending from the proximal end 106 to the distal end 104 of the elongate shaft 110 is provided. The lumen 130 is in fluid communication with the spiral hook 118, which in this example is preferably a hollow needle through which a fluid, such as a medicinal substance, may be injected. As such, the spiral hook 118 may function as an injection needle for the injection of various substances, such as anesthetics, into the cervix.

Of course, the cannulas 120 and 122 could be replaced by a single tube as discussed in more detail with reference to FIG. 3. As such, the various instruments could simply be housed within such a tube without the need for individual cannulas.

Figure 3:
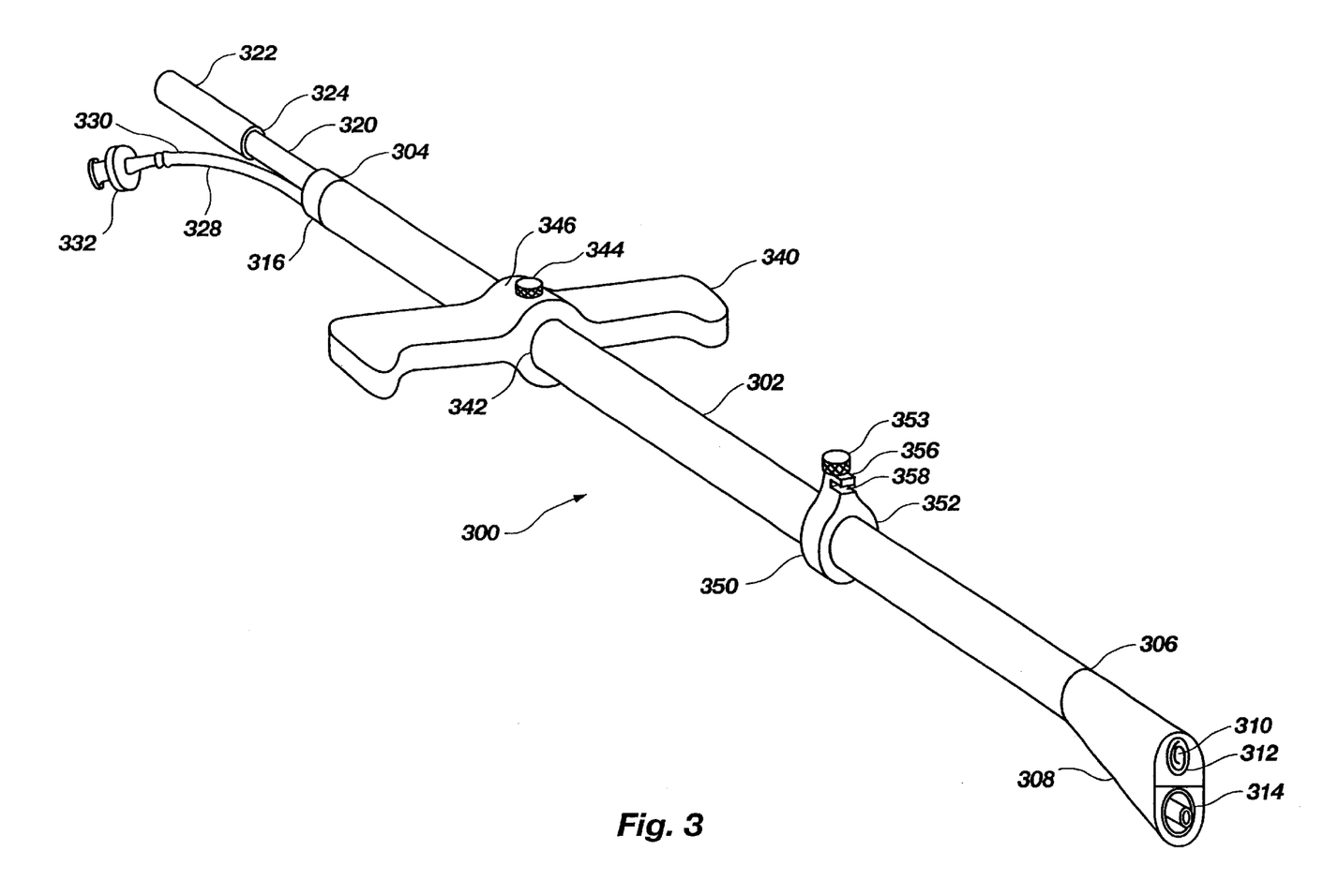
FIG. 3 is a perspective view of a third embodiment of a cervical retractor in accordance with the principles of the present invention.

FIG. 3 illustrates yet another preferred embodiment of a spiral cervical retractor, generally indicated at 300, in accordance with the principles of the present invention. The retractor 300 is comprised of an elongated tube 302 having a proximal end 304 and a distal end 306. A head member 308 is attached to the distal end 306 of the tube 302. The head member 308 is configured with an opening therein to house a spiral tipped rod 310 to which a spirally-shaped member 312 is attached. In addition, the head member 308 houses a luer lock fitting 314 to which an injection needle (not shown) having a similarly configured fitting can be mated therewith. The head member 308 is configured to angle the fitting 314 downwardly from the longitudinal axis of the tube 302. As such, any instrument, such as a hollow needle for injection of a drug, will be downwardly angled to make such an instrument more easily visible when the retractor has been inserted into the vaginal canal. Other instruments could also be attached to the fitting 314 such as a tube for providing suction or lavage, as may be the case when it is desired to take specimen samples from the area or a biopsy.

The proximal end 304 of the tube 302 is fitted with a base member 316. As will be shown and described in more detail, the base member 316 has a generally cylindrical shape to substantially match the diameter of the tube 302. The base member 316 is provided with a pair of apertures (not visible) formed therein. The first aperture is sized to receive an elongate rod 320 which runs the length of the tube 302 and may be coupled to or integrally formed with the wire tipped rod 310. The rod 320 is fitted with a gripping member 322 which fits over the distal end 324 of the rod 320 for gripping by a user, such as a gynecologist or other health care professional.

The other aperture in the base member 316 is configured for receiving a section of tubing 328 which runs the length of the tube 302 and is attached to the fitting 314. The proximal end 330 is also provided with a luer lock fitting 332 for attachment of a syringe (not shown) or other medical instrument having a luer lock fitting that can mate with the fitting 332. By attaching a tube to the fitting 314 at the distal end 306 of the tube 302 and attaching a syringe to the fitting 332, suction or lavage can be performed at the location of the head portion 308. That is, a saline solution could be injected through the tubing 328 to wash the area of tissue surrounding the head portion 308. Likewise, any fluids surrounding the head portion 308 could be suctioned through the tubing 328 by activation of a syringe attached to the fitting 332.

Manipulation of the tube 302 is further added by a handle member 340 which can be slid along the length of the tube 302 as desired. The handle member 340 defines a transversely extending bore 342 which is sized to receive the tube 302 with a relatively snug fit which still allows easy sliding of the handle member 340 along the tube 302. A set screw 344 orthogonally or threadedly engages a threaded hole (not visible) in the top surface 346 of the handle member 340. The set screw 344 is capable of retaining the handle member 340 in place at a desired location along the length of the tube 302.

A tube retaining member 350 comprises a slidable ring portion 352 which is configured to be slid along the tube 302 to any desire location. The retaining member 350 is provided with a set screw 353 similar in configuration to the set screw 344. The retaining member 350 thus includes a threaded bore (not visible) which extends through the top 356 of the retaining member 350 for receiving the set screw 352. Tightening of the set screw 353 causes the end of the set screw 352 to engage with the outer surface of the tube 302 thus holding the retaining member 353 in place.

The retaining member 350 also includes a transversely extending slot 358 which lies in a plane substantially parallel to a plane defined by the outer surface of the tube 302. The slot 358 is configured to fit within the notch provided on all standard speculums (not shown). By mating the slot 358 with the notch of the speculum, the tube 302 can be held in place relative to the speculum. As such, both hands of the health care professional can be freed while the spiral retractor 300 retains traction on the cervix of a patient.

Figure 4:
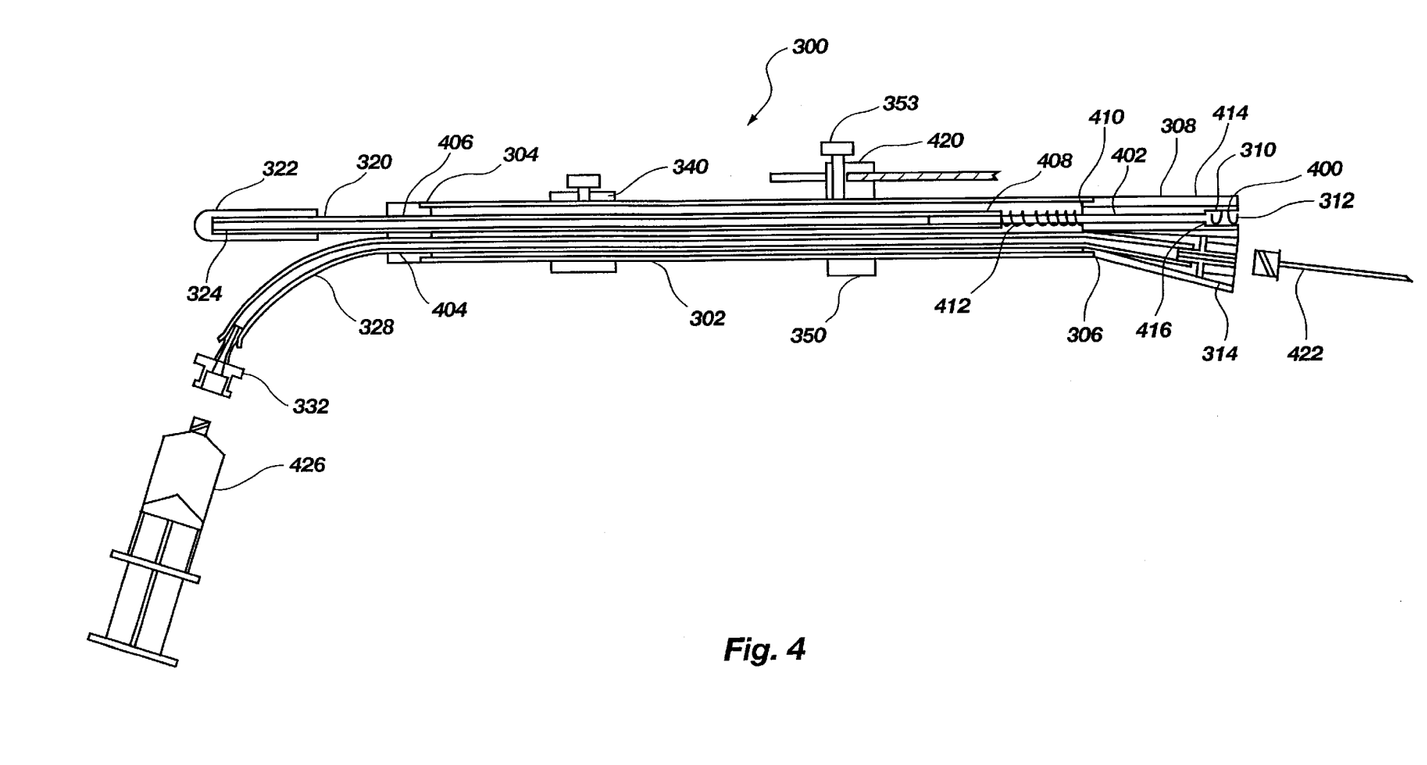
FIG. 4 is a cross-sectional side view of the cervical retractor illustrated in FIG. 3.

As further illustrated in FIG. 4, which shows a cross-sectional view of the spiral cervical retractor 300 shown in FIG. 3, the tube 302 is hollow and houses the various components of the instrument. The head portion 308 is partially fitted within the tube 302 so that the outer surface of the head portion substantially matches the contour of the tube along the joint between the head portion 308 and the tube 302. The head portion 308 houses the fitting 314, which may be held in place by friction fit, and the spiral wire 312 retaining member 310.

The spiral wire 312 is preferably formed by milling surgical steel into a coil and then sharpening the distal end. Approximately half of the coil is embedded in the retaining member 310 so that the spiral wire 312 cannot become dislodged in a patient. Preferably, the spiral wire 312 is molded into the retaining member 310. The retaining member 310 is a rod-like member which has a distal portion 400 having a diameter that is larger than the proximal portion 402. The proximal portion 402 extends through the head member 308 and into the elongate rod 320. The proximal portion 402 may be permanently attached to the rod 320 as by a plastic weld or an adhesive, or may be threaded into the rod to provide a means for a replaceable tip without having to discard the entire instrument. Thus, the rod 320 is preferably a hollow tube that extends out the proximal end 304 of the tube 302 for gripping by a user.

The base member 316, which is provided with apertures 404 and 406, retains the proximal portion of the tube 328 and allows the actuation and manipulation rod 320 to slide relative to the tube 302. The gripping member 322 is essentially a cap which extends over the proximal end 324 of the rod 320. As the proximal end of the coil retaining member 310 is inserted into the rod 320, the distal end 408 of the rod 328 and the proximal end 410 of the head member 308 provide abutment surfaces for a biasing member 412, such as a coil spring wrapped around the proximal portion 402 of the coil retaining member 310. The biasing member 412 forces or pulls the coiled wire 312 into the head portion 308. A tubular insert 414 fitted within the head portion 308 provides an abutment surface 416 so as to abut against the distal portion of the retaining member 310. As such, the retaining member 310 and thus the coiled wire 312 can only be pulled into the head portion 308 a predetermined distance. This distance is preferably just enough to retract the tip of the coil wire 312 into the head member 308.

When the gripping member 322 is forced toward the distal end 306 of the tube 302, the spring 412 is compressed between the rod 320 and the head portion 308, forcing the coiled wire 312 out of the head portion 308. Once the spiral wire 312 is projecting from the head portion 308, rotation of the gripping member 322 causes rotation of the rod 320 and thus the coiled wire 312. If the coiled wire 312 is engaging tissue when rotated it will pierce the tissue and thus become engaged with the tissue. By releasing the gripping member 322 at this point, the spring 412 will cause the wire 312 to retract back toward the head member 308, thus applying traction to the tissue. In order to remove the wire 312 from the tissue, the gripping member is simply rotated in the opposite direction to release the wire from the tissue.

During such a procedure, the handle member 340 is configured with a pair of gripping portions (see FIG. 3) which can be grasped with the index and middle fingers. The thumb can then be used to press against the gripping member 322 to force the wire 312 out the distal end of the instrument 300. Once the wire 312 is inserted into the tissue and traction is achieved, the speculum gripping member 350 can be slid onto a speculum 420 and the set screw 353 tightened to hold the tube 302 in place relative to the speculum 420.

As previously discussed, it is often desirable to provide a means for injecting a drug into the surrounding tissue near or at the location where traction is to be applied. As such, the head portion 308 is provided with a luer lock fitting 314 mounted therein. Of course those of skill in the art will appreciate that other types of fittings may be employed as well as other types of instruments and devices, such as those previously discussed herein. In this instance, however, the fitting 314 is configured to receive and retain a hollow needle 422 for drug injection purposes. As the health care professional inserts the needle into the vaginal canal, care must be taken to avoid pricking the walls of the canal. In addition, once the needle 422 is in position, the health care professional must be able to see the end of the needle to ensure that the injection is being given in the proper location. As such, the fitting 314 is downwardly angled approximately 15 to 20 degrees from the longitudinal axis of the tube 302. This also angles the needle so that upon visualizing inferior to the tube 302, the tip of the needle 422 should be visible. This would likely also be beneficial for other types of instruments that may be attached to the fitting 314. A syringe 426 may be attached to the fitting 332 to inject a drug solution through the tubing 328 and out the needle 422.

While the cervical retractor 300 shown in FIGS. 3 and 4 is capable of performing at least two primary functions simultaneously, those of skill in the art will appreciate that such an instrument may be configured to perform a single function, such as retraction only, or multiple functions such as retraction, suction, injection and illumination. Such multiple functionality could be achieved by fitting additional instruments or devices into the tube 302.

It is noteworthy that none of the prior art provides the combination of a skin hook device with an apparatus that can be inserted into the uterus with ease. Many women experience more pain from tenaculum placement than from the actual procedure the tenaculum is intended to facilitate (such as radiologic hysterosalpingograms). This invention will diminish the pain and morbidity of such commonly performed procedures.

In accordance with the features and combinations described above, a preferred method of cervical retraction includes the steps of:
(a) inserting a tube having a spiral hook attached to a distal end thereof into a vagina of a patient; and
(b) rotating a spiral hook on the end of the tube to place traction on the cervix for insertion or affixation of a medical instrument into the uterus of the patient or to a fetus.

It will be appreciated that the structure and apparatus disclosed herein is merely one example of a means for a spiral cervical retraction apparatus, and it should be appreciated that any structure, apparatus or system for a spiral cervical retraction apparatus which performs functions the same as, or equivalent to, those disclosed herein are intended to fall within the scope of a means for a spiral cervical retraction apparatus, including those structures, apparatus or systems for a spiral cervical retraction apparatus which are presently known, or which may become available in the future. Anything which functions the same as, or equivalently to, a means for a spiral cervical retraction apparatus falls within the scope of this invention. For example, the device may be configured with disposable tips which include the spiral hook, interchangeable spiral tips of varying strengths and wire diameters. In addition, the spiral cervical retractor may be provided in various lengths depending on the procedure to be performed. Furthermore, the spiral cervical retractor in accordance with the present invention may be provided with attachment features for attachment and/or fastened to a standard speculum to facilitate a variety of procedures.

It is to be understood that the above-described arrangements are only illustrative of the application of the principles of the present invention. Numerous modifications and alternative arrangements may be devised by those skilled in the art without departing from the spirit and scope of the present invention and the appended claims are intended to cover such modifications and arrangements. Thus, while the present invention has been shown in the drawings and fully described above with particularity and detail in connection with what is presently deemed to be the most practical and preferred embodiment(s) of the invention, it will be apparent to those of ordinary skill in the art that numerous modifications, including, but not limited to, variations in size, materials, shape, form, function and manner of operation, assembly and use may be made without departing from the principles and concepts set forth herein.

What is claimed is:

1. A spiral cervical retraction apparatus comprising;
an elongate member having a proximal end and a distal end;
a hook retaining member coupled to the elongate member proximate the distal end of the elongate member;
a spiral hook coupled to the hook retaining member; and
a biasing member coupled to said hook retaining member for retracting said spiral hook relative to the elongate member.

2. The apparatus of claim 1, wherein said hook retaining member is further configured for extending and retracting said spiral hook relative to said elongate member.

3. The apparatus of claim 2, wherein said elongate member comprises a tube, and further including an elongate rod extending within said tube, said rod having said hook retaining member coupled to a distal end thereof, and said rod having a proximal end for grasping and manipulating said spiral hook.

4. The apparatus of claim 1, wherein said elongate member further comprises a head member having a first opening formed therein for receiving said spiral hook therein when in a retracted position.

5. The apparatus of claim 4, wherein said head member further comprises a second opening for coupling an additional instrument thereto.

6. The apparatus of claim 5, further including a fitting inserted within said second opening, a section of tubing having a distal end secured to said fitting and extending through said elongate member to said proximal end thereof.

7. The apparatus of claim 6, further including a second fitting attached to a proximal end of said tubing.

8. The apparatus of claim 5, wherein said second opening is downwardly angled approximately twenty degrees from a longitudinal axis of said elongate member.

9. The apparatus of claim 5, wherein said additional instrument is comprised of one of a site illumination device, a site visualization device, a suction device and a lavage device.

10. The apparatus of claim 1, further including a handle member slidable along and securable relative to said elongate member.

11. The apparatus of claim 1, further including a speculum retaining member slidable along and securable relative to said elongate member.

12. A spiral cervical retraction apparatus comprising;
a tube having a proximal end and a distal end;
an elongate rod extending through said tube having a proximal end for grasping and manipulating by a user relative to said tube and a distal end;
a spiral hook coupled to said distal end of said elongate rod; and
a biasing member coupled to said rod for retracting said spiral hook relative to said tube.

13. The apparatus of claim 12, further including a hook retaining member coupled to said elongate rod for retracting said spiral hook into said tube.

14. The apparatus of claim 12, wherein said tube further comprises a head member having a first opening formed therein for receiving said spiral hook therein when in a retracted position.

15. The apparatus of claim 14, wherein said head member further includes a second opening for coupling an additional instrument coupled thereto.

16. The apparatus of claim 15, further including a fitting inserted within said second opening, a section of tubing having a distal end secured to said fitting and extending through said tube.

17. The apparatus of claim 16, further including a second fitting attached to a proximal end of said tubing.

18. The apparatus of claim 15, wherein said second opening is downwardly angled approximately twenty degrees from a longitudinal axis of said elongate member.

19. The apparatus of claim 15, wherein said additional instrument is comprised of one of a site illumination device, a site visualization device, a suction device and a lavage device.

20. The apparatus of claim 12, further including a handle member slidable along and securable relative to said tube.

21. The apparatus of claim 12, further including a speculum retaining member slidable along and securable relative to said tube.

22. A spiral cervical retraction apparatus comprising;
an elongate member having a proximal end and a distal end;
a hook coupled to said distal end of said elongate member and retractable relative to said elongate member; and
a head portion associated with said distal end of said elongate member having a first opening formed therein for receiving said hook when said hook is in a retracted position and a second opening for coupling an additional instrument thereto.

23. The apparatus of claim 22, further comprising a hook retaining member coupled to said elongate member, said hook attached to said hook retaining member and a biasing member coupled to said hook retaining member for retracting said hook into said first opening.

24. The apparatus of claim 22, wherein said elongate member comprises a tube, and further comprising an elongate rod extending within said tube, said hook coupled to a distal end of said rod and said rod having a proximal end for grasping and manipulating said hook.

25. The apparatus of claim 22, further including a fitting inserted within said second opening, a section of tubing having a distal end secured to said fitting and extending through said elongate member to said proximal end thereof.

26. The apparatus of claim 25, further including a second fitting attached to a proximal end of said tubing.

27. The apparatus of claim 22, wherein said second opening is downwardly angled approximately twenty degrees from a longitudinal axis of said elongate member.

28. The apparatus of claim 22, further including a handle member slidable along and securable relative to said elongate member.

29. The apparatus of claim 22, further including a speculum retaining member slidable along and securable relative to said elongate member.

30. The apparatus of claim 22, wherein said additional instrument is comprised of one of a site illumination device, a site visualization device, a suction device and a lavage device.

31. A spiral cervical retraction apparatus comprising;
an elongate member having a proximal end and a distal end;
a hook coupled to said distal end of said elongate member and retractable relative to said elongate member;
a head portion associated with said distal end of said elongate member having a first opening formed therein for receiving said hook when said spiral hook is in a retracted position; and
a speculum retaining member slidable along and securable relative to said elongate member.

32. The apparatus of claim 31, further comprising a hook retaining member coupled to said elongate member, said hook attached to said hook retaining member and a biasing member coupled to said hook retaining member for retracting said hook into said first opening.

33. The apparatus of claim 31, wherein said elongate member comprises a tube, and further comprising an elongate rod extending within said tube, said hook coupled to a distal end of said rod and said rod having a proximal end for grasping and manipulating said hook.

34. The apparatus of claim 31, wherein said head portion further comprises a second opening for coupling an additional instrument thereto.

35. The apparatus of claim 34, further including a fitting inserted within said second opening, a section of tubing having a distal end secured to said fitting and extending through said elongate member to said proximal end thereof.

36. The apparatus of claim 35, further including a second fitting attached to a proximal end of said tubing.

37. The apparatus of claim 34, wherein said second opening is downwardly angled approximately twenty degrees from a longitudinal axis of said elongate member.

38. The apparatus of claim 34, wherein said additional instrument is comprised of one of a site illumination device, a site visualization device, a suction device and a lavage device.

39. The apparatus of claim 31, further including a handle member slidable along and securable relative to said elongate member.

* * * * *